United States Patent [19]
Munk

[11] Patent Number: 5,608,517
[45] Date of Patent: Mar. 4, 1997

[54] FLOW CELL AND METHOD FOR MAKING SAME

[75] Inventor: Miner N. Munk, Sonoma, Calif.

[73] Assignee: Thermo Separation Products Inc., Fremont, Calif.

[21] Appl. No.: 395,784

[22] Filed: Feb. 28, 1995

[51] Int. Cl.[6] .................................................. G01N 21/05
[52] U.S. Cl. .......................................... 356/246; 356/440
[58] Field of Search ................................... 356/246, 440; 250/576

[56] References Cited

U.S. PATENT DOCUMENTS

| | | |
|---|---|---|
| 4,530,569 | 7/1985 | Squire . |
| 4,575,424 | 3/1986 | Allington et al. . |
| 4,754,009 | 6/1988 | Squire . |
| 4,867,559 | 9/1989 | Bach ........................................ 235/417 |
| 4,889,611 | 12/1989 | Blough, Jr. . |
| 4,973,142 | 11/1990 | Squire . |
| 4,975,505 | 12/1990 | Squire . |
| 4,977,025 | 12/1990 | Squire . |
| 4,999,248 | 3/1991 | Squire . |
| 5,000,547 | 3/1991 | Squire . |
| 5,006,382 | 4/1991 | Squire . |
| 5,076,659 | 12/1991 | Bekiarian et al. . |
| 5,184,192 | 2/1993 | Gilby et al. ............................. 356/246 |
| 5,267,341 | 11/1993 | Shearin .................................. 385/125 |
| 5,416,879 | 5/1995 | Liu ......................................... 385/125 |
| 5,444,807 | 8/1995 | Liu ......................................... 385/125 |

*Primary Examiner*—Richard A. Rosenberger
*Attorney, Agent, or Firm*—Killworth, Gottman, Hagan & Schaeff

[57] ABSTRACT

A coated flow cell and a method for making the coated flow cell are provided. The flow cell comprises a flow passage internally coated with a polymer having an index of refraction lower than that of water. In this manner, light directed into the flow cell is internally reflected or "piped" down the length of the flow passage. As a result, flow cells having path lengths significantly longer and accepting incident angles of light much greater than possible with prior art flow cells. A method for internally coating the flow cell is also provided.

25 Claims, 4 Drawing Sheets

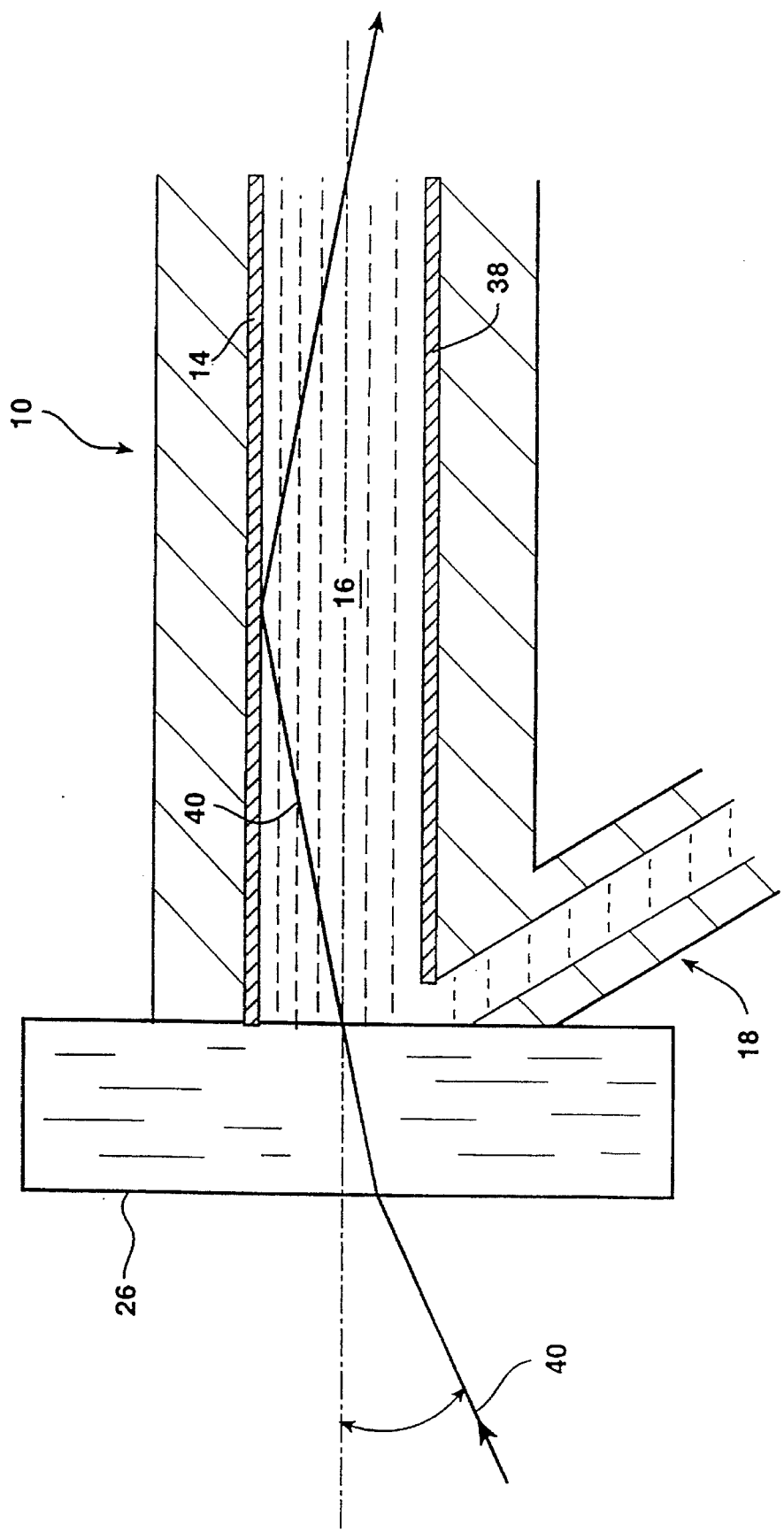

FLOW CELL AND METHOD FOR MAKING SAME

BACKGROUND OF THE INVENTION

This invention relates to a flow cell for light absorption measurement, and more particularly, to a flow cell coated with a polymer having an index of refraction below that of water. This flow cell has special application in the well established techniques of high performance liquid chromatography (HPLC) and capillary zone electrophoresis (CZE).

Light absorption detectors for HPLC and CZE generally comprise four basic components: a light source, a means for selecting a narrow increment of wavelengths, a flow cell, typically in the form of a hollow tube, through which a sample to be analyzed and the light are passed, and a light sensor which measures the amount of light transmitted through the flow cell. When a light absorbing component passes through the flow cell, the amount of light transmitted through the flow cell decreases in accordance with Beer's law;

$$\frac{I}{I_o} = 10^{-\alpha bc} \quad \text{(Beer's Law)}$$

where I is the transmitted light power, $I_o$ is the light power incident on the flow cell, $\alpha$ is the molar absorptivity of the sample, b is the pathlength of the light in the flow cell (in centimeters), and c is the sample concentration (in moles per liter). The detector output is usually in terms of Absorbance (A) which is defined as the product $\alpha$ b c and is proportional to both the sample concentration, c, and the pathlength, b. The longer the pathlength, the larger the detector output signal for a given sample concentration. In conventional flow cells, light that strikes the lateral wall of the flow cell is partially lost due to absorption and scattering at the wall. This lost light causes an increase in noise in the output signal of the detector. The lateral dimension or diameter of the flow cell can be increased to reduce the fraction of light striking the lateral wall, but this increases the volume of the flow cell in the proportion to the diameter squared. A larger cell volume results in spreading out or dispersion of a sample peak and loss in chromatographic resolution in HPLC and a similar loss in resolution in CZE. In practice, this loss in resolution limits conventional flow cells to pathlengths of the order of 6 to 10 mm for HPLC and even shorter for CZE because of the narrower sample peaks or smaller peak volumes associated with CZE.

Accordingly, it has long been desired to produce flow cells capable of longer pathlengths without an excessive increase in light loss or cell volume. This desire may be realized by coating the inside wall of the flow cell with a low refractive index polymer so that light striking the coated wall is total internally reflected back in to the cell bore, and light-piped along the cell bore. The basic requirement for light-piping is that the refractive index of the internal wall coating be less than that of the liquid in the flow cell. Water has the lowest refractive index in the UV range of the spectrum for wavelengths between 190 nm and 300 nm of liquids commonly used in HPLC and CZE, so the refractive index of the coating should be less than that of water. A further requirement of the coating is that it is reasonably transparent at the wavelengths used in the measurement of light absorption in the flow cell. While light does not propagate in the coating when total internally reflected, an evanescent wave is established along the surface that will absorb light power if the coating material is not transparent.

Light-piping in a liquid is not a new concept. Commercial liquid light pipes are available, but these usually contain a high refractive index liquid so that polymer coating of TEFLON TFE and TEFLON FEP both of which are available from DuPont Polymers of Wilmington, Del., will effectively light pipe. However, these long available polymers will not effectively light pipe in low refractive index liquids like water as their indices of refraction are greater than that of water.

U.S. Pat. No. 4,575,424 discloses flow cells for light absorption detectors which are internally coated with rhodium which is polished to a mirror finish. However, the flow cell coating is a rather expensive material which requires complicated manufacturing techniques to give a highly polished surface on the inside of a narrow bore. Further, rhodium is not a perfect electrical conductor, and, consequently, there is some absorption of light upon reflection.

Accordingly, the need remains for a flow cell useful for low refractive index liquids which is inexpensively and easily coated with a material having an index of refraction lower than that of water which totally internally reflects light along the cell bore.

SUMMARY OF THE INVENTION

This need is met by the present invention whereby a flow cell having a coating which substantially totally internally reflects light along the cell bore and a method for making the same are provided. The coated flow cell of the present invention comprises a cell having a flow passage internally coated with a polymer having an index of refraction lower than that of water. In this fashion, light directed into the cell is reflected down the length of the flow cell, in other words "piped", without substantial loss of light through the walls of the flow passage. As a result, flow cells having longer path lengths and narrower bores than possible in the prior art may be manufactured. This allows for the greater sensitivity in a light absorption detector employing the flow cell of the present invention.

In accordance with one aspect of the present invention, a coated flow cell for light absorption measurement is provided. The flow cell comprises a housing having an interior wall defining a flow passage through the housing. The flow passage has an inlet and outlet through which a liquid phase sample to be analyzed is directed. The housing has a first end and a second end, both of which have transparent windows through which light may be directed.

The interior wall of the housing is internally coated with a polymer having an index of refraction lower than that of water. The coated interior wall reflects light directed into the flow passage, thereby piping the light through the flow passage. In this manner, flow cells of greater length and narrower bores than in the prior art are possible. Preferably, the polymer is 1,3 dioxole-4,5 difluoro-2,2 bis trifluoromethyl polymer with tetrafluoroethane.

The flow cell of the present invention may have a flow passage of about 10 mm or longer while having a diameter of less than about 1 mm. Preferably, the flow cell of the present invention is at least about 50 mm in length while having a diameter of less than about 1 mm. The flow cell is capable of internally reflecting or piping at least about 80% and preferably 90% of the light directed into the flow passage. Additionally, the interior wall may be coated with said polymer to a thickness of at least about 0.1 mm to assure complete coverage of the surface. The thickness need only be of the order of the wavelength of light for total internal reflection.

In accordance with another aspect of the present invention, a light absorption detector for the analysis of chemicals in the liquid phase is provided. The light absorption detector comprises the flow cell as described above, a light source for directing light into the flow cell and a detection device for detecting the amount of light passing through the flow cell.

In accordance with an additional aspect of the present invention, a process for producing a coated flow cell is provided. The process comprises providing a housing having an interior wall defining a flow passage. The flow passage has an inlet and outlet through which a liquid phase sample to be analyzed is directed. The housing has a first end and a second end, both of which have transparent windows through which light may be directed. The process further includes internally coating the interior wall of the housing with a polymer having an index of refraction lower than that of water.

The interior wall of the housing may be coated by providing a mandrel externally coated with the polymer. The coated mandrel is then placed into the flow passage of the housing. Heat is then applied to the housing to adhere the polymer to the housing wall and the mandrel is removed leaving the polymer adhered to the interior wall of the housing.

The housing is preferably polytetrafluoroethylene, and more preferably polytetrafluoroethylene with a layer of a copolymer of tetrafluoroethylene and hexafluoroethylene as the interior wall. The mandrel may be removed by either dissolving the mandrel or by polishing the mandrel before the polymer is coated on it, then pulling the mandrel out of the flow passage once the polymer is adhered to the interior wall.

Alternatively, the interior wall of the housing may be coated by deposition of the polymer from solution. In such a process, a deposition solution is provided by dissolving the polymer in a liquid solvent. The flow passage is then filled with the deposition solution. The solvent is then evaporated to deposit a chemically inert coating of the polymer on the interior wall. To facilitate coating of the interior wall the housing may be rotated while submerged in the deposition solution. Preferably, the solvent is a fluorosilane and the polymer 1,3 dioxole-4,5 difluoro-2,2 bis trifluoromethyl polymer with tetrafluoroethene.

In yet another embodiment of the present invention, a coated flow cell for light absorption is again provided. The flow cell comprises a housing having an interior wall defining a flow passage through the housing. The flow passage has an inlet and outlet through which a liquid phase sample to be analyzed is directed. The housing has a first end and a second end, both of which have transparent windows through which light may be directed. The flow passage has a diameter of less than about 1 mm with an acceptance half angle of light of at least about 10°, preferably at least about 15°.

At least a portion of the interior wall of said housing is internally coated with a polymer having a lower index of refraction than water, such as 1,3 dioxole-4,5 difluoro-2,2 bis trifluoromethyl polymer with tetrafluoroethane. The coated interior wall reflects light directed into the flow passage thereby piping light through the flow passage.

Accordingly, it is a feature of the present invention to provide a flow cell which is internally coated with a polymer having an index of refraction lower than that of water and having acceptance angles of light of at least 10°. It is further a feature of the present invention to provide a light absorption detector incorporating the flow cell of the present invention. It is yet further a feature of the present invention, to provide a process for making the flow cell of the present invention.

BRIEF DESCRIPTION OF THE DRAWINGS

FIG. 4 is a schematic view of light entering the flow cell of the present invention.

DETAILED DESCRIPTION OF THE PREFERRED EMBODIMENTS

Figure 1:
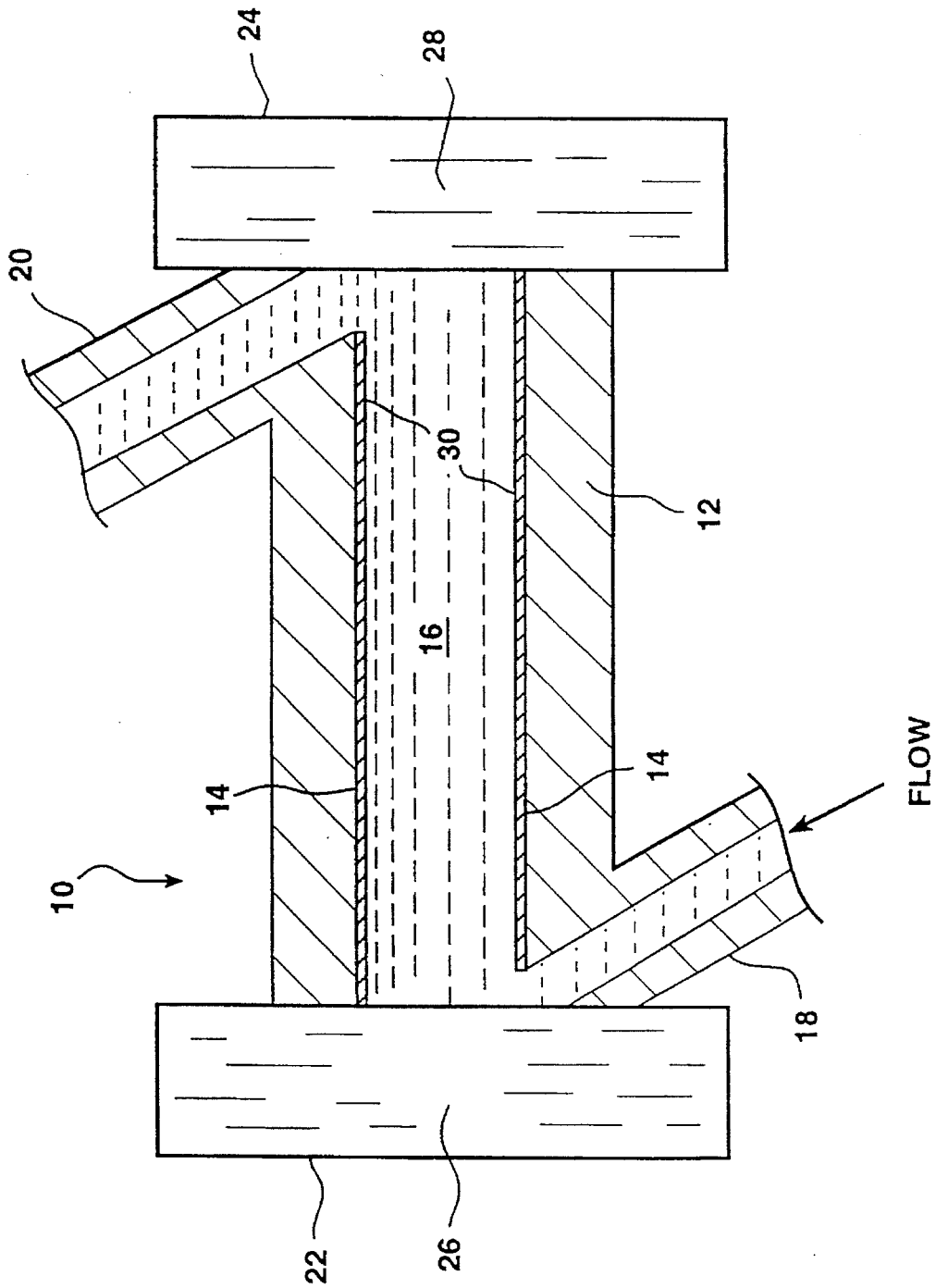
FIG. 1 is schematic view of the coated flow cell according to the present invention.

The present invention provides a coated flow cell that is superior in directing light from a source through a sample and to a detector than flow cells of the prior art. Turning to FIG. 1, the coated flow cell 10 of the present invention is depicted. Flow cell 10 comprises a housing 12 having an interior wall 14 defining a flow passage 16. Typically, flow passage 16 will be a cylindrically-shaped bore. Flow cell 10 includes an inlet 18 through which a sample to be analyzed enters flow passage 16. The flow cell 10 also includes an outlet 20 through which the sample exits the flow cell 10. One of ordinary skill in the art will recognize that flow cell 10 can take various other shapes and geometries besides that depicted in FIG. 1.

The housing 12 of flow cell 10 also includes a first end 22 and a second end 24. First end 22 includes a first transparent window 26 through which light is directed into the flow passage 16 from a source (not shown). Second end 24 also includes a transparent window 28 through which light departs the flow passage 16. Transparent windows 26 and 28 may be constructed of any suitable material, such as quartz, fused silica or transmitting optical fibers which is known in the art for providing transparency. Furthermore, transparent windows 26 and 28 may be of any size or shape known in the art, such as a slit. Of course, one of ordinary skill in the art will recognize that the size, shape or material used in transparent windows 26 and 28 will depend upon end use considerations as well as the detector into which the flow cell is incorporated.

To provide the unique design of the present invention, polymer 30 having an index of refraction lower than that of water is coated onto interior wall 14 of housing 12. As a result, light which is directed into the flow passage 16 at angles up to a certain acceptance angle is totally internally reflected by the interior wall 14. The light is reflected down the length of flow passage 16, or in other words, the light is piped. In this fashion, substantially less light is lost through the walls of the housing than in conventional flow cells. The coated flow cell 10 of the present invention internally reflects or pipes at least about 80% of the light directed into the flow passage 16. Preferably, the flow cell 10 of the present invention internally reflects at least about 90% of the light directed into the flow cell. Preferably, the polymer is coated to a thickness greater than at least about 0.1 mm to assure complete coverage.

Since flow cell 10 of the present invention pipes light down the flow passage 16, substantially longer and narrower flow passages or path lengths are possible with the flow cell of the present invention. Further, as light is piped down the flow passage, there is no requirement that the flow passage be straight as in prior art flow cells. Rather, the flow passages of the cell 10 of the present invention may contain curves or bends, thereby contributing advantages to detector design.

The present invention provides for substantially longer path lengths or flow passages than flow cells of the prior art without increasing cell volume. Due to piping of light down the flow passage, the flow cells of the present invention are substantially longer and narrower than conventional flow cells. Thus, increased sensitivity is gained without substantially increase in background noise or substantial loss of peak resolution in the detector. Flow passages 16 of 10 mm or longer with bore diameters of less than about 1 mm, preferably about 0.5 mm are achievable. Preferably, the flow passage is 25 mm in length while having a diameter of less than about 1 mm. More preferably, the flow passage of the present invention is at least about 50 mm in length while having a diameter of at less than about 1 mm.

Returning to FIG. 1, polymer 30 has an index of refraction lower than that of water. Water has a lower refractive index than other solvents commonly used in HPLC and CZE for UV wavelengths of primary interest, i.e., wavelengths between 190 nm and 300 nm. If light of these wavelengths can be light piped through a flow cell filled with water, it can be light piped with other common liquids in the flow cell as well. Thus, housing 12 is internally coated with a polymer having an index of refraction lower than that of commonly used solvents in the wavelength range of primary interest between 190 nm and 300 nm. A suitable polymer having an index of refraction below that of water is 1,3 dioxole-4,5 difluoro-2,2 bis trifluoromethyl polymer with tetrafluoroethane, available from Dupont Polymers of Wilmington, Del. under the tradename TEFLON AF. Two versions of TEFLON AF include TEFLON AF 1600 with an index of refraction of 1.305 at a wavelength of 589 nm and TEFLON AF 2400 with an index of refraction of 1.294 at a wavelength of 589 nm. TEFLON AF is both ultraviolet and visible light transparent and capable of being deposited from solution which greatly increase the ease of applicability.

As a result of the piping of light, the flow cell of the present invention provides for superior acceptance of incident half angles of light. The incident half angle of light is the half angle at which light may be directed into the first transparent window 26. In other words, it is the half angle at which light may be directed into flow passage 16. The expression determining light piping is:

$$\sin \theta_0 < \sqrt{n_L^2 - n_C^2} \qquad (2)$$

where $\theta_o$ is the half angle of incidence of the light entering the first transparent window, $n_L$ is the refractive index of the liquid in the cell and $n_c$ is the refractive index of the coating on the flow cell.

As $n_L$ for the present invention is greater than no, it can be seem from FIG. 4 that light 40 will be internally reflected or piped down the length of flow passage 16. It can also be seen that the flow cell 10 will accept much greater incident half angles of light $\theta_o$ in the narrower cell widths preferred for the present invention than prior art cells of the same geometry. Prior art flow cells of the same geometry, due to loss of light through the cell wall and a lack of light piping, must have light enter a flow cell with a narrow bore almost parallel to the flow passage at incident half angles of about 0.5° or less. Whereas, the flow cell 10 of the present invention may accept incident half angles of light $\theta_o$ of at least about 10° and preferably of at least about 15°. As a result, when employing the flow cell 10 of the present invention, significantly more light enters the flow passage 16 then in prior art flow cells, thereby increasing sensitivity. Furthermore, more flexibility in detector design is provided when employing the flow cell of the present invention.

The flow cell 10 of the present invention may be employed in conventional light absorption detectors known in the art. Flow cell 10 may be employed in both uv/visible monochromatic detectors employing a photodiode detector and in uv/visible polychromatic detectors employing diode array detectors. However, due to a desire for narrower cell bores for use with diode array detectors, flow cell 10 of the present invention is uniquely suited for use in conjunction with diode array detectors. Examples of suitable light absorption detectors include the Hitachi L-4500 (trademark) photodiode array detector, available from Hitachi Corp. of San Jose, Calif., the Hewlett-Packard 1090 (trademark) photodiode array detector available from Hewlett-Packard Corp. of Palo Alto, Calif., and the Perkin-Elmer 480 (trademark) photodiode detector available from Perkin-Elmer Corp. of Wilton, Conn.

Figure 2:
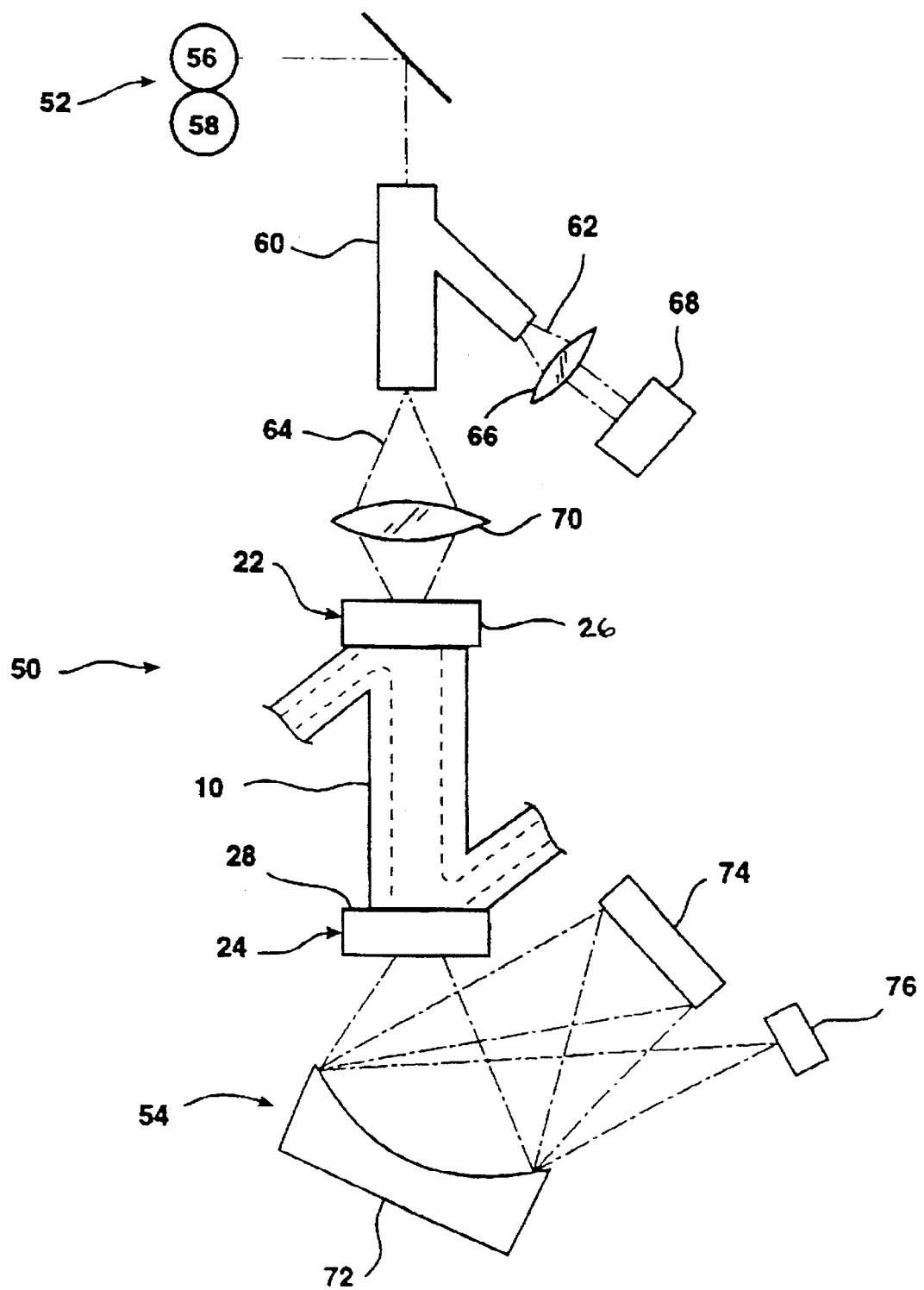
FIG. 2 is a schematic view of the light absorption detector of the present invention.

Turning to FIG. 2, a preferred uv/vis diode array detector of the present invention is shown. Although not depicted to scale, FIG. 2 shows a uv/vis detector 50 employing flow cell 10 from FIG. 1. The detector 50 includes a light source 52 adjacent the first end 22 of the flow cell for directing light through first transparent window 26. Detector 50 also includes a detection device 54 positioned adjacent the second end 24 of the flow cell 10 for detecting the light passing through second transparent window 28.

Light source 52 includes a uv light source 56 and a visible light source 58. Light sources 56 and 58 are typically conventional deuterium lamps, tungsten halogen lamps, or both. Emission-line lamps may also be substituted for special applications or as calibration sources. A combined beam of light generated from light sources 56 and 58 is passed through a beam splitter 60. Beam splitter 60 splits the generated beam of light into two portions of light 62 and 64 sending first portion 62 through lens 66 to reference diode 68 while sending the second portion 64 through lens 70 to flow cell 10.

Once passing through flow cell 10, the second portion of light 64 is received by detection device 54. Detection device 54 comprises a grating 72. Grating 72 disperses second portion of light 64 into different wavelengths. As the light will emerge from flow cell 10 at included angles of up to about 25°, a fast grating, such as one with a P/No. on the order of about 2.2 is required. Such gratings are commercially available, from for example Instruments S.A.

The dispersed beam of light is then focused on a conventional photodiode array detector 74. Array detector 74 includes multiple photodiodes (not shown). In this fashion, each photodiode in the array can detect the intensity of different wavelengths of light absorbed while passing through flow cell 10. Suitable array detectors includes a 512 or 1024 element array, available from Hamanatsu Inc. If so desired, an additional reference diode 76, commonly called a zero order diode, may be employed to monitor changes in light transmission through flow cell 10 due to changes in temperature and refractive index of the fluid in the cell.

This flow cell can also be employed in monochromatic detectors, which use a single photodiode to measure absorbance at a selected range of wavelengths. A grating, placed before or after the flow cell is rotated to select the desired wavelength.

The flow cell 10 of the present invention is produced by internally coating the interior wall 14 of housing 12 with a polymer having a lower index of refraction than water. The interior wall 14 may be coated by dissolving the polymer in a suitable solvent, filling the flow passage 16 with the polymer solution and drying the flow cell 10 to deposit polymer on the interior wall 14. If desired, the housing 12 and, thus, flow passage 16 may be rotated during deposition so as to deposit a more uniform coating. Again the polymer is preferably TEFLON AF while the suitable solvent is a fluorosilane such as FLUORINERT solvent available from the 3M Company of Minneapolis, Minn.

Figure 3A:
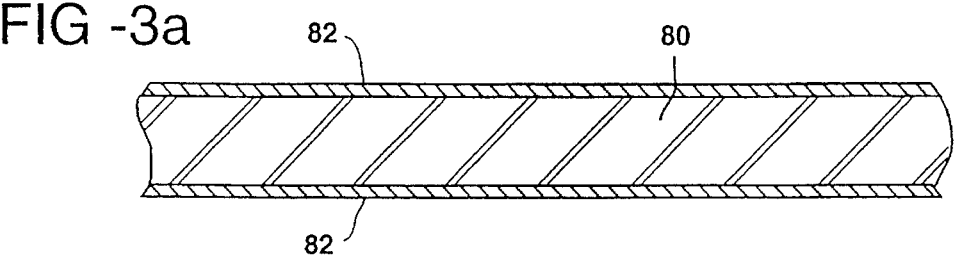
FIG. 3a–3d are schematic representations of the steps of the preferred process for coating the flow cell of the present invention.

An alternative and preferred process for coating the flow cell of the present invention is shown in FIGS. 3a–3d. Turning to FIG. 3a, a mandrel 80 externally coated with a polymer 82, such as TEFLON AF, having an index of refraction lower than that of water is provided. Mandrel 80 may be constructed of a material that can be polished to a smooth finish and has reasonable mechanical strength and integrity at temperatures up to 340° C. The mandrel can be a thin walled aluminum tube that can be chemically dissolved from the wall structure after forming to leave the internally exposed TEFLON AF coating. Alternately, the mandrel can be a more chemically inert material such as 304 stainless steel where the mandrel is removed from the formed wall structure by pulling it out of bore. In this case a slightly tapered mandrel can be used to facilitate the pulling out of the mandrel.

The mandrel can be coated by multiple dipping and drying of the mandrel into a solution of TEFLON AF dissolved in FLUORINERT solvent. When a sufficient thickness of TEFLON AF has been deposited, the coating is cured by heating the coated mandrel to about 340° C. and slowly cooling it to ambient temperature.

Figure 3B:
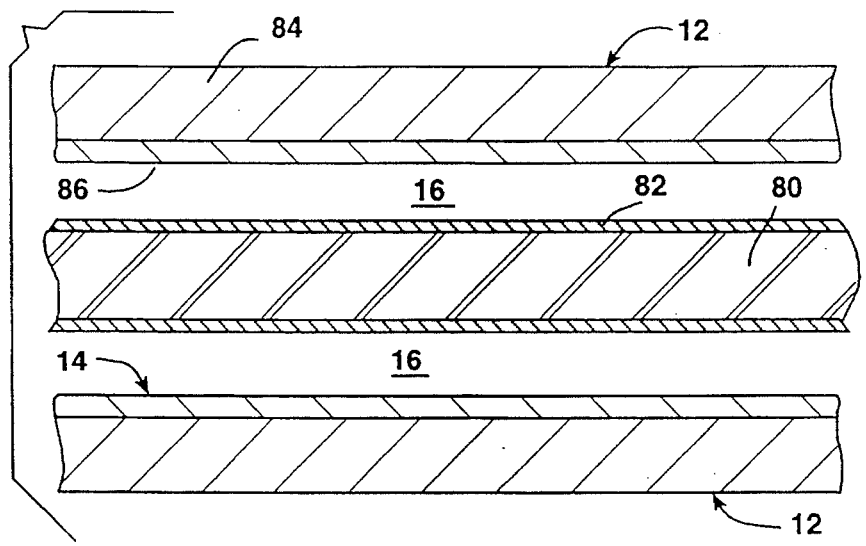

Turning next to FIG. 3b, the coated mandrel 80 is inserted into flow passage 16. Housing 12 comprises heat shrinkable, polytetrafluoroethylene tubing. Preferably, the housing comprises an outer layer 84 of tetrafluoroethylene homopolymer, known as TEFLON-TFE available from Dupont Polymers of Wilmington, Del. and an inner layer 86 of tetrafluoroethylene copolymer with hexafluoropropylene, known as TEFLON-FEP also available from Dupont Polymers of Wilmington, Del., as interior wall 14.

Figure 3C:
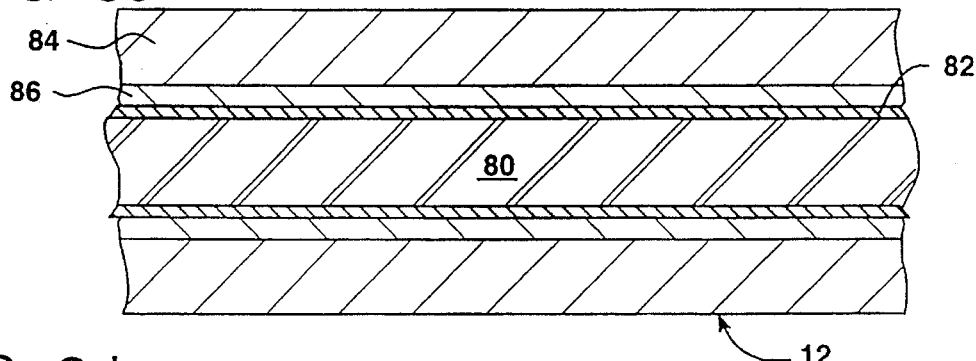
Figure 3D:
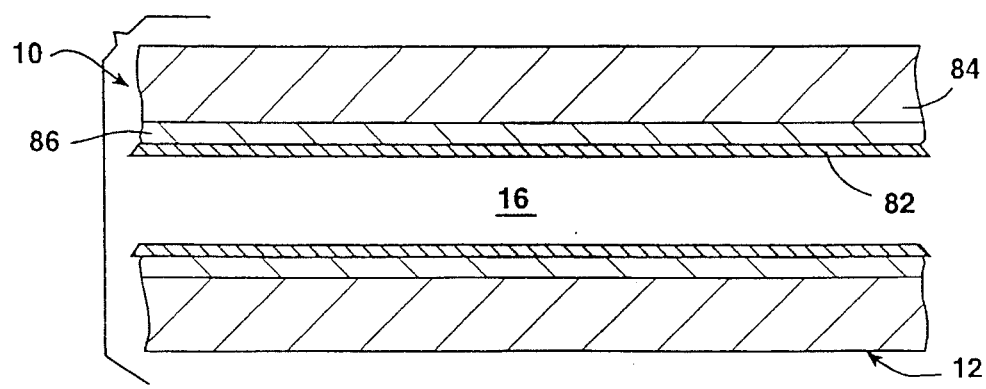

The housing 12 may also comprise a dual-shrink tubing. A suitable assembly is then heated to shrink the outer layer 84 and to melt the inner layer 86. The melting inner layer 86 fuses to the polymer layer 82 on mandrel 80 upon cooling, as shown in FIG. 3c. Mandrel 80 is then removed from flow passage 16 as shown in FIG. 3d, leaving polymer layer 82 fused and bonded to inner layer 86. The end product is a flow cell 10 internally coated with a polymer having an index of refraction lower than that of water according to the present invention. Mandrel 80, if aluminum, may be removed by dissolution in strong alkaline solution such as sodium hydroxide. Alternatively, if polished, mandrel 80 may be removed by pulling the mandrel 80 from flow passage 16.

Having described the invention in detail and by reference to the preferred embodiment thereof, it will be apparent that modifications and variations are possible without departing from the scope of the invention which is defined in the appended claims.

What is claimed is:

1. A flow cell for light absorption measurement comprising:

a housing comprising an outer layer of a heat shrinkable polymer and an inner layer of a second polymer, said inner layer of said second polymer forming an interior wall defining a flow passage, said flow passage having an inlet and an outlet through which a liquid phase sample to be analyzed is directed, said housing having a first end and a second end, said first and second ends having transparent windows through which light is directed, and at least a portion of said interior wall having bonded thereto a polymer having an index of refraction lower than that of water.

2. The flow cell as claimed in claim 1 wherein said coated interior housing wall internally reflects light directed into the flow passage thereby piping said light through said flow passage.

3. The flow cell as claimed in claim 1 wherein said flow passage is about 10 mm or longer while having a diameter of less than about 1 mm.

4. The flow cell as claimed in claim 3 wherein said coated interior housing wall internally reflects at least about 80% of light directed into the flow passage.

5. The flow cell as claimed in claim 1 wherein said interior wall of said housing is internally coated with said polymer to a thickness of at least about 0.1 mm.

6. The flow cell as claimed in claim 3 wherein said flow passage is at least about 50 mm in length while having a diameter of less than about 1 mm.

7. The flow cell as claimed in claim 1 wherein said interior housing wall is coated with 1,3 dioxole-4,5 difluoro-2,2 bis trifluoromethyl polymer with tetrafluoroethene.

8. The flow cell as claimed in claim 1 in which said heat shrinkable polymer comprises a homopolymer of tetrafluoroethylene.

9. The flow cell as claimed in claim 1 in which said second polymer comprises a copolymer of tetrafluoroethylene with hexafluoropropylene.

10. A light absorption detector for the analysis of chemical compounds in the liquid phase comprising:

a flow cell comprising a housing, said housing comprising an outer layer of a heat shrinkable polymer and an inner layer of a second polymer, said inner layer of said second polymer forming an interior wall defining a flow passage, said flow passage having an inlet and an outlet through which a liquid phase sample to be analyzed is directed, said housing having a first end and a second end, said first and second ends having first and second transparent windows through which light is directed, and at least a portion of said interior wall having bonded thereto a polymer having an index of refraction lower than that of water, a light source positioned adjacent said first end of said flow cell housing for directing light through said first transparent window and into said flow passage, and, a detection device positioned adjacent said second end of said flow cell housing for detecting light passing through said flow passage and said second transparent window.

11. The detector as claimed in claim 10 wherein said flow passage is at least about 15 mm in length while having a diameter of less than about 1 mm.

12. The detector as claimed in claim 11 wherein said coated interior housing wall internally reflects light directed into the flow passage from said light source thereby piping said light through said flow passage.

13. The detector as claimed in claim 12 wherein said coated housing wall internally reflects at least about 80% of light directed into the flow passage.

14. The detector as claimed in claim 10 wherein said interior wall of said housing is internally coated with said polymer to a thickness of at least about 0.1 mm.

15. The detector as claimed in claim 10 wherein said housing comprises tetrafluoroethylene.

16. The detector as claimed in claim 10 wherein said interior wall of said housing is coated with 1,3 dioxole-4,5 difluoro-2,2 bis trifluoromethyl polymer with tetrafluoroethene.

17. The flow cell as claimed in claim 10 in which said heat shrinkable polymer comprises a homopolymer of tetrafluoroethylene.

18. The flow cell as claimed in claim 10 in which said second polymer comprises a copolymer of tetrafluoroethylene with hexafluoropropylene.

19. An internally coated flow cell for light absorption measurement comprising:

a housing comprising an outer layer of a heat shrinkable polymer and an inner layer of a second polymer, said inner layer of said second polymer forming an interior wall which defines a flow passage, said flow passage having bonded thereto a material with a refractive index less than a liquid confined by said flow passage, said flow passage having an inlet and an outlet through which a liquid phase sample to be analyzed is directed, said housing having a first end and a second end, said first and second ends having transparent windows through which light is directed, and an acceptance half angle for light of at least about 10°.

20. The flow cell as claimed in claim 19 wherein at least a portion of said interior wall of said housing is internally coated with a polymer having an index of refraction lower than that of water.

21. The flow cell as claimed in claim 20 wherein said coated interior wall of said housing internally reflects light directed into the flow passage thereby piping said light through said flow passage.

22. The flow cell as claimed in claim 20 wherein said interior wall of said housing is coated with 1,3 dioxole-4,5 difluoro-2,2 bis trifluoromethyl polymer with tetrafluoroethene.

23. The flow cell as claimed in claim 19 wherein said flow passage accepts incident half angles of light of at least about 15°.

24. The flow cell as claimed in claim 19 in which said heat shrinkable polymer comprises a homopolymer of tetrafluoroethylene.

25. The flow cell as claimed in claim 19 in which said second polymer comprises a copolymer of tetrafluoroethylene with hexafluoropropylene.

\* \* \* \* \*